US011001620B2

(12) United States Patent
Sung et al.

(10) Patent No.: US 11,001,620 B2
(45) Date of Patent: May 11, 2021

(54) COMPOSITION COMPRISING RECOMBINANT HUMAN THYROID STIMULATING HORMONE AND METHOD FOR PRODUCING RECOMBINANT HUMAN THYROID STIMULATING HORMONE

(71) Applicants: GENEXINE, INC., Seongnam-si (KR); PROGEN CO., LTD., Seoul (KR)

(72) Inventors: Young Chul Sung, Seoul (KR); Zungyoon Yang, Incheon (KR)

(73) Assignee: PROGEN CO., LTD., Seoul (KR)

( * ) Notice: Subject to any disclaimer, the term of this patent is extended or adjusted under 35 U.S.C. 154(b) by 137 days.

(21) Appl. No.: 15/773,855

(22) PCT Filed: Nov. 4, 2016

(86) PCT No.: PCT/KR2016/012633
§ 371 (c)(1),
(2) Date: May 4, 2018

(87) PCT Pub. No.: WO2017/078451
PCT Pub. Date: May 11, 2017

(65) Prior Publication Data
US 2019/0062396 A1   Feb. 28, 2019

(30) Foreign Application Priority Data

Nov. 5, 2015   (KR) .................. 10-2015-0154882

(51) Int. Cl.
| *C07K 14/59* | (2006.01) |
| *G01N 33/76* | (2006.01) |
| *G01N 33/574* | (2006.01) |
| *A61K 38/24* | (2006.01) |
| *A61K 51/02* | (2006.01) |

(52) U.S. Cl.
CPC .............. *C07K 14/59* (2013.01); *A61K 38/24* (2013.01); *A61K 51/025* (2013.01); *G01N 33/574* (2013.01); *G01N 33/76* (2013.01)

(58) Field of Classification Search
None
See application file for complete search history.

(56) References Cited

U.S. PATENT DOCUMENTS

| 6,117,991 A | 9/2000 | Wondisford et al. |
| 2003/0198596 A1 | 10/2003 | Kourides et al. |
| 2010/0210512 A1* | 8/2010 | Kelly ............. A61K 38/24 514/6.9 |
| 2012/0315217 A1 | 12/2012 | Gershengorn et al. |

FOREIGN PATENT DOCUMENTS

| CN | 105002242 A | 10/2015 |
| JP | 4501802 A | 4/1992 |
| JP | 2013525284 A | 6/2013 |
| KR | 10-1983-0007087 A | 10/1983 |
| WO | 2012091124 A1 | 7/2012 |

OTHER PUBLICATIONS

Kumar et al., Cytotechnology. Apr. 2007;53(1-3):33-46 (Year: 2007).*
Japanese Patent Office, Communication dated May 7, 2019 issued in Application No. 2018-542093.
Daniella C. Ventini, et al., "Improved Bioprocess with CHO-hTSH Cells on Higher Microcarrier Concentration Provides Higher Overall Biomass and Productivity for rhTSH", Applied Biochemistry and Biotechnology, 2011, pp. 401-409, vol. 164.
Stephen Blamey, et al., "Using Recombinant Human Thyroid-Stimulating Hormone for the Diagnosis of Recurrent Thyroid Cancer", Australian and New Zealand Journal of Surgery, 2005, pp. 10-20, vol. 75.
Mohamed B. Al-Fageeh, et al., "The Cold-Shock Response in Cultured Mammalian Cells: Harnessing the Response for the Improvement of Recombinant Protein Production", Biotechnology and Bioengineering, 2006, pp. 829-935, vol. 93.
Korean Office Action for Application No. 10-2015-0154882 dated Jun. 21, 2017.
International Search Report for PCT/KR2016/012633 dated Jan. 13, 2017 [PCT/ISA/210].

* cited by examiner

Primary Examiner — Daniel C Gamett
(74) Attorney, Agent, or Firm — Sughrue Mion, PLLC (57) ABSTRACT

The present invention relates to a composition for the diagnosis and treatment of recurrent thyroid cancer comprising recombinant human thyroid stimulating hormone (rhTSH) and a method for producing the recombinant human thyroid hormone. The method for producing recombinant human thyroid hormone according to the present invention can effectively produce rhTSH despite being cultured through fed-batch culture, and has a high purification yield and purity. Therefore, the recombinant thyroid stimulating hormone produced by the method can be usefully used for the diagnosis or treatment of recurrent thyroid cancer.

13 Claims, 8 Drawing Sheets

Specification includes a Sequence Listing.

Figure 2A. Viable cell density & Productivity

Figure 2B. Viability

Figure 5A. Purification summary

| Purification Step / Item | Purification Yield (%) | Purity (%) | HCP (ppm) | Note |
|---|---|---|---|---|
| Harvest culture media | 100 | 65 | 91314 | 1. For the pharmaceutical use, HCP should be less than 100ppm<br><br>2. Due to the broad range of PI in TSH, it is very difficult to remove HCP within the limits of its allowed amount |
| UF/DF | 96 | 73 | 45790 | |
| Nuvia Q (Capture) | 78 | 88 | 22590 | |
| Depth filtration | 75 | 90 | 27571 | |
| Blue 6 FF (Intermediate polishing) | 45 | 94 | 4230 | |
| Phenyl HP (Polishing) | 34 | 95 | 2090 | |
| Q membrane | 30 | 100 | 974 | |
| Formulation (Diafiltration) | 29 | 98.73 | 623 | |

Figure 5B. SDS-PAGE

Lanes 1, 2: Reference
Lanes 3, 4: Purified rhTSH

Figure 6A. Purification summary

| Purification Step | Item | Purification Yield (%) | Purity (%) | HCP (ppm) | Note |
|---|---|---|---|---|---|
| Harvest culture media | | 100 | . | 98,000 | 1. HCP: within the limits<br><br>2. Purification yield: 60% increase<br><br>3. Purification steps: Shorten from 7 to 5 |
| CaptureSelect Gonadotropin | | 63 | 100 | 121 | |
| Depth filtration | | 58 | 100 | 62 | |
| Diafiltration | | 56 | 100 | 49 | |
| Capto adhere | | 45 | 100 | 17 | |
| Formulation (Diafiltration) | | 45 | 100 | 12.5 | |

Figure 6B. SDS-PAGE

Lanes 1, 2: Reference
Lanes 3, 4: Purified rhTSH

Figure 7A. Gel IEF

Lanes 1, 2: Reference
Lanes 3, 4: Purified rhTSH

Figure 7B. Peptide mapping (Trypsin treatment)

Figure 8A. In vitro assay

Figure 8B. In vivo assay

COMPOSITION COMPRISING RECOMBINANT HUMAN THYROID STIMULATING HORMONE AND METHOD FOR PRODUCING RECOMBINANT HUMAN THYROID STIMULATING HORMONE

CROSS REFERENCE TO RELATED APPLICATIONS

This application is a National Stage of International Application No. PCT/KR2016/012633, filed on Nov. 4, 2016, which claims priority from Korean Patent Application No. 10-2015-0154882, filed on Nov. 5, 2015.

TECHNICAL FIELD

The present invention relates to a composition comprising a recombinant human thyroid stimulating hormone and a method for producing the recombinant human thyroid stimulating hormone.

BACKGROUND ART

Thyroid stimulating hormone (TSH) is secreted from the hypothalamus through the anterior pituitary gland and is related to various mechanisms such as general growth of tissues including the nervous system, stimulation of basal metabolic rate, production and secretion of growth hormone and prolactin, hormonal activity, an increase in glucose reabsorption, increases in mitochondrial oxidation/phosphorylation, activity of the adrenal medulla, induction of enzymatic synthesis, etc. To activate a specific signaling pathway, TSH binds to the TSH receptor of thyroid follicular cells in the thyroid gland and induces the production and secretion of two hormones called T3 (triiodothyronine) and T4 (thyroxine) that mediate the above-mentioned mechanisms. In addition, TSH consists of two subunits, and the two subunits refer to an α subunit including 92 amino acids and a β subunit including 118 amino acids.

The prevalence of thyroid cancer across the world continues to increase. In the United States for 30 years from 1980 to 2010, the number of thyroid cancer patients increased by 6 times whereas in Korea, for 20 years from 1990 to 2010, that increased by approximately 18 times. In the United States, the number of thyroid cancer patients is expected to increase by approximately 3.5 times for 20 years from 2010 to 2030, while that of other major cancer patients is expected to remain stable or decrease slightly during the same period.

When thyroid cancer is diagnosed, most of the treatment therefor involves complete removal of the thyroid tissue from the patient. Patients who undergo thyroidectomy must be administered with T3 and T4, which are thyroid hormones, to maintain thyroid function for the rest of their lives. In the treatment of these thyroid cancers, follow-up examinations are very important to prevent the recurrence and metastasis of cancer due to residual tissues after thyroidectomy. For the diagnosis to confirm the recurrence of early-stage thyroid cancer, although the presence of recurrence is confirmed by quantifying the thyroglobulin protein in the blood after long-term interruption of the administration of T3 and T4, such method will induce various side effects such as hypothyroidism because it stops the administration of T3 and T4 for a while. Thus, in the last two decades, without stopping the administration of the hormones, T3 and T4, the methods of diagnosing the recurrence of thyroid cancer by quantifying the thyroglobulin protein in the blood within 2 to 3 days after administering recombinant human thyroid stimulating hormone (rhTSH) are widely used.

Moreover, rhTSH can be concurrently used to increase the absorption rate of radioactive isotopes (iodine) for therapeutic purposes when the residual thyroid tissue is removed from thyroidectomized patients so that recurrent thyroid cancer can be effectively treated without side effects.

However, at present, rhTSH on the market creates a large burden on consumers due to low productivity and purification yield. As such, while carrying out research to increase the productivity and purification yield of rhTSH, the inventors of the present invention established optimum culturing and purifying conditions for the production of rhTSH, thereby completing the present invention.

DISCLOSURE OF INVENTION

Technical Problem

An object of the present invention is to provide a composition for treatment or diagnosis of recurrent thyroid cancer comprising recombinant human thyroid stimulating hormone produced by the method of the present invention.

Another object of the present invention is to provide a method for producing recombinant human thyroid stimulating hormone by fed-batch culturing.

Solution to Problem

In order to achieve the above object, the present invention provides a composition for diagnosis or treatment of recurrent thyroid cancer, comprising recombinant human thyroid stimulating hormone (rhTSH) as an active ingredient, which is obtained through fed-batch culturing, comprising culturing a cell line producing rhTSH at a culture temperature 35° C. to 40° C.; culturing the cell line by lowering the culture temperature to the range from 29° C. to 34° C., when the number of cultured cells reaches $3\times10^6$ to $2\times10^7$ cells/mL; and obtaining rhTSH from the culture solution.

In order to achieve another object mentioned above, the present invention provides a method for producing recombinant human thyroid stimulating hormone by fed-batch culturing, comprising culturing a cell line producing rhTSH at a culture temperature 35° C. to 40° C.; culturing the cell line by lowering the culture temperature to the range from 29° C. to 34° C., when the number of cultured cells reaches $3\times10^6$ to $2\times10^7$ cells/mL; and obtaining rhTSH from the culture solution.

Advantageous Effects of Invention

The method for producing recombinant human thyroid stimulating hormone according to the present invention can efficiently produce rhTSH despite culturing by fed-batch culturing and has high purification yield and purity. Therefore, the recombinant thyroid stimulating hormone produced by the above method can be effectively used for the diagnosis and treatment of recurrent thyroid cancer.

BRIEF DESCRIPTION OF DRAWINGS

FIGS. 2A and 2B are graphs showing the viable cell density and productivity (FIG. 2A) and the viability (FIG.

2B) of the cells selected to confirm the optimum temperature in the production of rhTSH. In the productivity graph of FIG. 2A, each bar represents 37° C.→33° C., 37° C., 37° C.→35° C., and 37° C.→31° C. of the culture temperature from the left.

BEST MODE FOR CARRYING OUT THE INVENTION

Hereinafter, the present invention will be described in detail.

The present invention provides a composition for diagnosis or treatment of recurrent thyroid cancer, comprising recombinant human thyroid stimulating hormone (rhTSH) as an active ingredient, which is obtained through fed-batch culturing, the culturing comprising culturing a cell line producing rhTSH at a culture temperature 35° C. to 40° C.; culturing the cell line by lowering the culture temperature to the range from 29° C. to 34° C., when the number of cultured cells reaches $3 \times 10^6$ to $2 \times 10^7$ cells/mL; and obtaining rhTSH from the culture solution.

As used herein, the term "recombinant human thyroid stimulating hormone (rhTSH)" is a protein secreted from the hypothalamus through the anterior pituitary gland and consists of an α subunit including 92 amino acids and a β-subunit including 118 amino acids. rhTSH is used as an adjuvant for the diagnosis and treatment of recurrent thyroid cancer patients. The recombinant human thyroid stimulating hormone according to the present invention may comprise an α subunit consisting of an amino acid sequence represented by SEQ ID NO: 1 and a β subunit consisting of an amino acid sequence represented by SEQ ID NO: 2.

The composition for the diagnosis or treatment of recurrent thyroid cancer, comprising rhTSH produced and purified according to the method of the present invention may be used to diagnose the recurrence of the tumor tissue after thyroidectomy or may be concurrently used with iodine isotopes for the treatment of recurrent thyroid cancer. The rhTSH which is used for the treatment of recurrent thyroid cancer may be used as an adjuvant for the anticancer treatment for iodine isotopes.

The rhTSH may further comprise a pharmaceutically acceptable carrier. The pharmaceutically acceptable carrier may be any carrier as long as it is a nontoxic substance suitable for delivery into a patient. Distilled water, alcohol, lipids, waxes, and inert solids may be included as a carrier. Pharmaceutically acceptable adjuvants (for example, buffering agents and dispersing agents) can also be included in the pharmaceutical composition.

The rhTSH of the present invention can also be administered to a subject in various ways. For example, the composition may be administered parenterally, examples of which include subcutaneous, ophthalmic, intraperitoneal, intramuscular, oral, rectal, intraorbital, intracerebral, intracranial, intravertebrally, intraventricularly, intrathecally, intracisternally, intracapsularly, intranasally, and intravenously. Specifically, the composition may be administered intramuscularly. The route of administration of the composition can be determined in consideration of fluid volume, viscosity, etc. depending on the administration method.

When administered parenterally as described above, the composition preferably comprises a part of an aqueous or physiologically acceptable body fluid suspension or solution. Accordingly, a physiologically acceptable carrier or transporting material can be added to the composition and delivered to the patient, which does not adversely affect the electrolyte and/or volume balance of the patient. Therefore, as a body fluid substance for the composition, physiological saline solution is generally included.

The above administration can be administered once or more, from one to three times, and more specifically, it can be administered in two divided doses. When the composition of the present invention is administered repeatedly, it can be repeatedly administered at intervals of 12 to 48 hours or 24 to 36 hours, and specifically at a 24-hour interval.

Such composition can be sterilized by conventionally well-known sterilization techniques. In addition, the composition according to the present invention may also comprise pharmaceutically acceptable auxiliary substances and adjuvants, toxicity-regulating preparations and analogs thereof which are required for adjusting physiological conditions such as pH, and examples thereof include sodium acetate, sodium chloride, potassium chloride, calcium chloride, sodium lactate, etc. The concentration of rhTSH that can be included in the composition may vary.

The unit dosage of the composition according to the present invention may be 0.6 to 1.2 mg, specifically 0.8 to 1.0 mg, more specifically 0.9 mg, based on the adult. The unit dosage may vary depending on the disease to be treated and the presence or absence of side effects, and the optimum dose can be determined through routine experimentation.

The composition according to the present invention may be used together with an iodine isotope for the diagnosis and treatment of recurrent thyroid cancer. In this case, the iodine isotope can be administered 12 to 36 hours, 18 to 30 hours, or 20 to 25 hours after administration of the composition according to the present invention. Specifically, it can be administered after 24 hours.

Meanwhile, the diagnosis of recurrent thyroid cancer may be performed through diagnostic scanning or serum thyroid globulin (Tg) examination after the administration of the composition of the present invention and the iodine isotope. In this case, the diagnostic scanning can be performed 24 to 60 hours, 36 to 54 hours, or 46 to 50 hours after administration of the iodine isotope. Specifically, it can be performed after 48 hours. Collection of serum specimens for serum thyroid globulin testing may be performed for 48 to 96 hours, 60 to 84 hours, or 70 to 74 hours, after administration of the iodine isotope, and specifically after 72 hours.

To prepare the composition of the present invention, the present invention comprises a step of culturing a cell line producing rhTSH at 35 to 40° C.

The cell line producing rhTSH according to the present invention may be a cell line having expression vectors including the above-mentioned α subunit and β subunit, and the above α subunit and β subunit may be prepared so as to be contained in each vector or in one vector, each subunit is expressed by its respective promoter (dual vector) or connected via an internal ribosome binding site (IRES) and prepared to be individually expressed. According to one specific embodiment of the present invention, it can be prepared to be individually expressed via IRES.

As used herein, the term "vector" refers to a nucleic acid means including a nucleotide sequence which can be introduced into a host cell and recombined and inserted into the host cell genome, or spontaneously replicated into an episome. Suitable expression vectors include expression control elements such as promoters, start codons, stop codons, polyadenylation signals, and enhancers, as well as signal sequences or leader sequences for membrane targeting or secretion, and they can be prepared variously according to the purpose. When a gene construct encoding a target protein is administered to a subject, a start codon and stop codon should definitely exhibit activity and be in frame in the coding sequence.

As used herein, the term "dual vector" refers to a vector in which two genes in one vector are regulated by their respective promoters and can independently express a target protein. In addition, the vector may include a marker capable of selecting a cell transformed with a target protein, and according to a specific embodiment of the present invention, the marker may be DHFR.

For the production of TSH showing activity, the α subunit and the β subunit must form a dimer. In this case, the expression level of the β subunit should be 3 to 4-fold higher than that of the α subunit to form an α/β dimer with high efficiency in cells. Therefore, at the time of preparing the expression vector, the promoter may be selected so that the expression level of the β subunit is high. According to a specific embodiment of the present invention, by connecting the β subunit to the CMV promoter and connecting the β subunit and the α subunit via an internal ribosome binding site (IRES), the expression level of the two subunits may be adjusted.

According to another aspect of the present invention, the present invention provides a host cell or a non-human host subject comprising the vector. The host cell or non-human host subject may be useful in a medical/pharmaceutical environment, as well as a method for obtaining the rhTSH of the present invention.

A host cell or non-human host subject which is transfected or transformed with a vector according to an embodiment of the present invention may be a host cell or a non-human host subject genetically modified by the vector. As used herein, the term "genetically modified" means to that a host cell, a non-human host subject, a predecessor, or a parent includes a polynucleotide or vector according to an embodiment of the present invention, which is introduced into the host cell, non-human host subject, predecessor, or parent, in addition to its own genome. Moreover, the polynucleotide or vector according to an embodiment of the present invention may exist in a genetically modified host cell or a non-human host subject as an external independent molecule outside the genome, specifically as a replicable molecule, or may be stably inserted into the genome of a host cell or non-human host subject.

A host cell according to an embodiment of the present invention is a eukaryotic cell. The eukaryotic cell includes a fungus, a plant cell, or an animal cell. An example of a fungus may be a yeast, specifically, a yeast of *Saccharomyces* sp., and more specifically, *S. cerevisiae*. In addition, examples of animal cells include insect cells or mammalian cells, and specific examples of animal cells include HEK293, 293T, NSO, CHO, MDCK, U2-OSHela, NIH3T3, MOLT-4, Jurkat, PC-12, PC-3, IMR, NT2N, Sk-n-sh, CaSki, C33A, etc. The host cells, for example, CHO cells may provide post-translational modification for the rhTSH protein according to one embodiment of the present invention, including removal of the leader peptide, glycosylation of the molecule at precise locations, and secretion of functional molecules. In addition, suitable cell lines well known in the conventional technical field may be obtained from an organization for cell line deposit such as American Type Culture Collection (ATCC).

In addition, CHO cells comprising a polynucleotide according to an embodiment of the present invention are particularly useful as host cells. When CHO cells are used as host cells, secondary modifications such as glycosylation and phosphorylation may occur in rhTSH.

The non-human host subject may be a non-human mammal, in particular, a mouse, a rat, a sheep, a calf, a dog, a monkey, and an ape.

The rhTSH according to the present invention may be expressed in various types of organisms such as bacteria, yeast, mammalian cells, plants, transgenic animals. However, mammalian cells can be used in view of the regulation of protein therapeutic agents and the fact that the prepared protein should be similar to the native form. Examples of the mammalian cells include immortal hybridoma cells, NS/O myeloma cells, 293 cells, Chinese hamster ovary cells (CHO cells), HeLa cells, CapT cells (human amniotic fluid-derived cells), COS cells, etc. According to a specific embodiment of the present invention, CHO cells may be used.

In order to introduce the expression vector according to the present invention into the above cell line, conventional techniques known in the technical field can be used, examples of which include electroporation, the plasmogamy method, the calcium phosphate ($CaPO_4$) precipitation method, and the calcium chloride ($CaCl_2$) precipitation method.

In the CHO cell according to the present invention, the dihydrofolate reductase (DHFR) gene, which is an essential enzyme for the synthesis of purine and thymidylic acid, is knocked down in order to select a cell line transformed with an expression vector. The DHFR-negative CHO cell is HT (hypoxanthine and thymidine), which is a mixture form of sodium hypoxanthine and thymidine, and it cannot grow without being provided with purine and pyrimidine. Thus, the cell line which is not transformed with an expression vector including the DHFR gene cannot survive in a medium not including HT.

In addition, in the present invention, a cell line producing rhTSH is cultured through fed-batch culturing conditions.

rhTSH has been produced by a conventional "perfusion culture", which is a method of continuously removing a used culture medium while continuously supplying a fresh culture medium. Such perfusion culture has disadvantages of a relatively low productivity, complex process and high costs.

As used herein, the term "fed-batch culture" refers to a culturing method in which the culture solution is not withdrawn from a culture container until the end of the culture while gradually adding a nutrition medium to the culture container during the progress of the culture. The method has an advantage in that the concentration of a component may be adjusted to an arbitrary set value during the culture by making the addition rate of a specific substance proportional to the consumption rate by the microorganism.

As used herein, the term "culture medium" refers to a nutrient solution for the maintenance, growth, proliferation, or expansion of cells in an artificial in vitro environment of a multicellular organism or outside the tissue. The culture medium may be optimized for specific cell cultures, examples of which include a basic culture medium prepared for the support of cell growth, or a basic culture medium prepared to promote the production of monoclonal antibodies, and a concentrated medium in which nutrients are concentrated at a high concentration.

The "basic culture medium" refers to a minimal medium capable of supporting cell growth. The basic culture medium supplies standard inorganic salts such as zinc, iron, magnesium, calcium, and potassium, as well as trace elements, vitamins, energy sources, buffer systems, and amino acids. The basic culture medium according to the present invention is used at the initial stage of culture, when is the growth phase of cells. Examples of the basic culture medium include DMEM, MEM, RPMI 1640, F-10, F-12, Hycell CHO, etc. According to a specific embodiment of the present invention, the basic culture medium can be a Hycell CHO medium.

The step of culturing a cell line at 35° C. to 40° C. in the fed-batch culture according to the present invention is during the growth phase of cells. This is a period when the growth of cells is rapidly progressed after inoculation of cells, and in general, culture conditions for cell growth may vary depending on the type of cells, the type of target proteins to be produced, etc. It is known that in the case of CHO cells used in the present invention, the number of cells increases most actively at a temperature of 35° C. to 37° C., and a pH range of 6.8 to 7.3. Meanwhile, the growth phase of cells in the fed-batch culture of the present invention may be 3 to 7 days, specifically 4 to 6 days from the initial stage of the culture. According to a specific embodiment of the present invention, the growth phase of the cells may be 6 days from the initial stage of the culture.

The culture temperature in the growth period may be 35° C. to 40° C. or 36° C. to 38° C., and according to one specific embodiment of the present invention, it may be 37° C. When cells are cultured at a temperature outside the above temperature range, cell growth may not occur well.

In addition, the present invention includes a step of culturing cells by lowering the culture temperature to the range from 29° C. to 34° C., when the number of cultured cells reaches $3\times10^6$ to $2\times10^7$ cells/mL.

When the culture temperature of the cells is lowered according to the fed-batch culture method of the present invention, the cells enter the production stage of proteins under culture conditions to maximize the production of the target protein. The culture conditions may be changed when the density of the viable cells density of which are cultured in the growth phase of cells to enter the production stage of proteins is approximately 60 to 90%, specifically, 70 to 80% of the maximum viable cell density. According to a specific embodiment of the present invention, the culture condition is changed when the viable cell density is approximately 70%.

In this case, the culture temperature of cells may be 29° C. to 34 ° C. or 31° C. to 33° C. According to one embodiment of the present invention, the culture temperature may be 33° C. When the culture temperature is 35° C. or higher, the viability of the cell sharply decreases, and when it is 28° C. or lower, there is a problem that the production rate of rhTSH decreases because the number of cells does not sufficiently increase.

In the fed-batch culture according to the present invention, the change of the culture temperature may be carried out when the number of cells is $3\times10^6$ to $2\times10^7$ cells/mL, $5\times10^6$ to $1\times10^7$ cells/mL, or $6\times10^6$ to $8\times10^6$ cells/mL. According to one embodiment of the present invention, the culture temperature may be changed when the number of cells is $6\times10^6$ cells/mL. If the culture temperature is changed when the number of cells is $3\times10^6$ cells/mL or less, the number of cells is so small that the amount of the obtained protein is small. When the number of cells is greater than $2\times10^7$ cells/mL, although the number of cells is large thereby the amount of the produced protein is large, HCP such as cell debris, etc. is also produced in a large quantity, and there is a problem in that it is difficult to remove HCP to a concentration corresponding to the pharmaceutical standards in the purification process.

The change of the culture temperature according to the present invention may be carried out on day 5 to day 9 of the culture, specifically on day 5 to day 8 of the culture, more specifically on day 5 to day 7 of the culture. According to a specific embodiment of the present invention, it may be carried out on day 6.

As used herein, the term "viable cell density" refers to the amount or number of living cells within a given space. In the present invention, the cell viable density is measured in order to change the culture conditions when an adequate number of cells are alive to produce the target protein with high efficiency. The cell viable density may be determined by measuring the absorbance of cells.

In addition, in the fed-batch culture of the present invention, a supplement may be supplied to a basic culture medium for protein production. As used herein, the term "supplement" refers to a substance that is additionally included in a basic culture medium for supplying abundant nutrients to maintain health and produce proteins when cells enter the protein production phase, and includes lipids, amino acids, vitamins, growth factors, etc. The types of supplements that can be used for the production of proteins are well known in the conventional technical field and include ActiCHO (GE Healthcare), Cell Boost (GE Healthcare), FM (Functional MAX, Gibco), yeast extract, Phytone UF (BD Biosciences), DM19, PP3, TC Yeastolate UF (BD Biosciences), etc. The above supplement may be ActiCHO, Cell Boost, and FM.

The supplement may be added in an appropriate amount for the production of high levels of recombinant proteins, and these supplements may be used either individually or mixed. The supplement may be added upon which cells pass through the growth phase and enter the phage of protein production, and according to the fed-batch culture of the present invention, it may be added 1 to 3 days before the temperature is lowered for the protein production. According to one specific embodiment of the present invention, it may be added 1 day before. The supplement should be continuously added because it is consumed for cell viability and in the protein production process. Generally, supplements may be added regularly at an interval of 1 to 3 days from the 1st day of the addition. Addition of supplements may vary depending on the amount and type of cells, culture conditions, etc., and it may be easily selected by those skilled in the art.

The culture for producing rhTSH according to the present invention may be maintained for 10 to 20 days, specifically 11 to 15 days, and more specifically 12 to 18 days. According to a specific embodiment of the present invention, it may last for 12 days.

The present invention also includes a step of obtaining rhTSH from a culture solution.

In order to obtain rhTSH from the culture solution, it may be obtained by purification of rhTSH by commonly well-known methods. However, in order to obtain rhTSH in a higher yield by purification, rhTSH may be obtained by a step of obtaining a primary purified solution by purifying in a column filled with a resin bound to the anti-gonadotropin antibody; a step of obtaining a secondary purified solution by passing the primary purified solution through a filter; a step of obtaining a tertiary purified solution by dialyzing the secondary purified solution; and a step of obtaining rhTSH by purifying the tertiary purified solution by ion chromatograph.

In general, rhTSH has a wide range of PI values and three N-glycosylation sites, and, thereby the removal of impurities during purification is not easy. Conventional rhTSH purification methods involve complex procedures due to a series of procedures of filtration, anion exchange chromatography, affinity chromatography, and hydrophobic interaction chromatography, which is not only costly and time consuming, but also there is a problem in that the level of impurities (for example, host cell proteins) purified by the above method is 1,000 ppm or more, which is higher than the permissible level (100 ppm) of impurities that can be contained in proteins for use in pharmaceutical applications of. Therefore, the present inventors established a purification method with a high yield and purity of rhTSH.

As used herein, the term "culture solution" refers to a culture medium, which comprises various factors including proteins produced and secreted from cells after cells are cultured. It can be obtained by removing cells by centrifuge after the completion of the culture.

As used herein, the term "affinity chromatography" is one of chromatography methods for using one of two types of substances having biologically high specific affinity as a stationary phase and separating a target substance using differences in affinity for the stationary phase. Therefore, in the above step, the culture solution may be purified by a column filled with a resin bound to the anti-gonadotropin antibody.

The resin used for the affinity chromatography consists of a matrix, a hydrophilic crosslinking agent, and a ligand. Here, the matrix may be cross-linked agarose, for example, highly cross-linked high-flow agarose. The ligand may be an anti-gonadotropin antibody, which is a protein that specifically binds to rhTSH of the present invention. In the resin, an antibody that specifically binds to rhTSH is covalently bound to an agarose fragment and may selectively bind to rhTSH. In addition, since the ligand has a long hydrophilic crosslinking agent in the resin, the target protein to be separated may easily bind. An example of the resin is CaptureSelect which is commercially available from ThermoFisher Scientific (USA) as custom-designed media.

As used herein, the term "anti-gonadotropin antibody" refers to an antibody which recognizes an α subunit of rhTSH having an amino acid sequence of SEQ ID NO: 1 as an epitope and specifically binds thereto. As mentioned above, TSH consists of two subunits, of which the α subunit is commonly included in other gonadotropin hormones including TSH.

According to a specific embodiment of the present invention, rhTSH may be eluted with a sodium citrate solution in a column filled with a resin to which the anti-gonadotropin antibody is bound. The solution may be used at an appropriate concentration and pH, which may interfere with binding with anti-gonadotropin antibodies to the extent that it does not alter the quality and activity of the target protein. An appropriate concentration range of the solution may be 0.01 to 5 M, 0.03 to 1 M, 0.06 to 0.5 M, or 0.07 to 0.3 M. According to a specific embodiment of the present invention, the concentration of the solution may be 0.1 M. Meanwhile, an appropriate pH range may be 1 to 5, 2 to 4, or 2.5 to 3.5. According to a specific embodiment of the present invention, the pH of the solution may be 3.

Filtration may be carried out to remove impurities such as insoluble aggregates and host cell proteins (HCP) included in the primary purified solution obtained by the affinity chromatography and to further increase the purity of the target protein. In a specific embodiment of the present invention, the filtration may be depth filtration.

As used herein, the term "depth filtration" refers to filtration carried out using two or more filters of different-sized pores, which are installed on each layer. The size of the pores of the filter for depth filtration may be 0.001 to 30 μm, 0.005 to 25 μm, 0.015 to 15 μm, or 0.020 to 12 μm. In a specific embodiment of the present invention, the filter may have a pore size of 0.025 to 10 μm.

The Tris solution may be used for filtration, and the solution used in this case may be at an appropriate concentration and pH as described above. A suitable concentration of the Tris solution may be 1 to 300 mM, 10 to 200 mM, 20 to 100 mM, or 30 to 70 mM. According to a specific embodiment of the present invention, the concentration of the Tris solution may be 50 mM. Meanwhile, the appropriate pH of the Tris solution may be 6 to 12, 7 to 11, or 8 to 10, and according to a specific embodiment of the present invention, the pH may be 9.

As used herein, the term "diafiltration" refers to a step of dilution for removing or separating impurities in a sample depending on the molecular size, using a filter with small holes.

In the present invention, for diafiltration, a semi-permeable membrane having a pore size of 0.01 to 0.5 μm, 0.1 to 0.3 μm, or 0.2 to 0.25 μm may be used. According to a specific embodiment of the present invention, diafiltration is performed using a semipermeable membrane (Millipak 20, Millipore) with a pore size of 0.22 μm under a pressure of 1.0 bar or less, and it finishes when the conductivity of the filtered solution becomes 30.0 μS/cm or less.

The ion chromatography according to the present invention may purify with a column filled with a resin to which a compound having the structure represented by Chemical Formula 1 is bound:

[Chemical Formula 1]

[Chemical Formula 1]

As used herein, the term "ion chromatography" is a method of purification based on different affinities relative to the stationary phase in the column. The separation mechanism through an ion chromatography column is mainly based on ion exchange in which a cation or an anion exchange medium is bound, and competitive exchange occurs depending on the degree of affinity of a cation or an anion among mobile phases opposite to ions bound thereto.

A column filled with a resin to which the compound having the structure of Chemical Formula 1 is bound is a strong anion exchanger having a multimodal functionality. As used herein, the term "multiple functionality" means that interaction with various substances is possible. Therefore, the resin to which the compound having the structure of Chemical Formula 1 is bound interacts with various substances via ionic interaction, hydrogen bonding, hydrophobic interaction, etc. to remove impurities such as HCP, aggregates, etc.

The target protein passed through the anion exchange chromatography may be eluted with a sodium acetate solution, and the solution used in this case may be at an appropriate concentration and pH as described above. An appropriate concentration of the sodium acetate solution may be 1 to 200 mM, 5 to 100 mM, 10 to 50 mM, or 15 to 30 mM. According to a specific embodiment of the present invention, the concentration of the sodium acetate solution may be 20 mM. Meanwhile, the appropriate pH of the sodium acetate solution may be 2 to 6, 2.5 to 5, or 3 to 4, and according to one specific embodiment of the present invention, the pH may be 3.8.

In this case, the flow rate of the sodium acetate solution for elution may be in a range of 10 to 500 mL/min, 10 to 300 mL/min, 10 to 100 mL/min, or 10 to 50 mL/min. According to a specific embodiment of the present invention, the flow rate of the above sodium acetate solution may be 15 mL/min.

The finally purified rhTSH by all of the above steps may further go through a step of diafiltration into a suitable solution to retain the final protein product. The protein product storage solution should not alter the protein's quality and activity even if the protein is stored for a long period of time. Therefore, the storage solution for rhTSH protein according to the present invention may include sodium phosphate, mannitol, and sodium chloride.

The present invention provides a method for producing recombinant human thyroid stimulating hormone by fed-batch culturing, comprising culturing a cell line producing rhTSH at a culture temperature of 35° C. to 40° C.; culturing cells by lowering a culture temperature to the range from 29° C. to 34° C., when the number of cultured cells reaches $3 \times 10^6$ to $2 \times 10^7$ cells/mL; and obtaining rhTSH from the culture solution.

The recombinant human thyroid stimulating hormone according to the present invention may include an α subunit consisting of an amino acid sequence represented by SEQ ID NO: 1 and a β subunit consisting of an amino acid sequence represented by SEQ ID NO: 2, and the general characteristics of producing the same are as described above.

Single cell clones selected according the method of the present invention were used to establish fed-batch culture conditions to more easily produce recombinant rhTSH.

The basic culture medium for cell culture is DMEM, MEM, RPMI 1640, F-10, F-12, Hycell CHO, etc. According to a specific embodiment of the present invention, the basic culture medium may be a Hycell CHO medium.

The step of culturing the cell line at 35° C. to 40° C. in the fed-batch culture according to the present invention is the growth period of the cell. The culture temperature in the above growth period may be 35° C. to 40 ° C. or 36° C. to 38° C., and according to one specific embodiment of the present invention, it may be 37° C. When cells are cultured at a temperature outside the above temperature range, there is a problem that cell growth does not occur well.

Depending on the fed-batch culture method according to the present invention, when the culture temperature of cells is lowered, the cells will enter the production phase of the protein under culture conditions to maximize the production of the target protein. In this case, the temperature may be 29° C. to 34° C. or 31° C. to 33° C. According to one embodiment of the present invention, the culture temperature may be 33° C. There is a problem that, when the culture temperature is 35° C. or higher, the viability of the cell sharply decreases, and when it is 28° C. or lower, the production rate of rhTSH decreases because the cells does not grow sufficiently.

In the fed-batch culture according to the present invention, changes of the culture temperature may be carried out when the number of cells is $3 \times 10^6$ to $2 \times 10^7$ cells/mL, $5 \times 10^6$ to $1 \times 10^7$ cells/mL, or $6 \times 10^6$ to $8 \times 10^6$ cells/mL. According to one embodiment of the present invention, the culture temperature may be changed when the number of cells is $6 \times 10^6$ cells/mL. If the culture temperature is changed when the number of cells is $3 \times 10^6$ cells/mL or less, the number of cells is so small that the amount of the obtained protein is small. When the number of cells is greater than $2 \times 10^7$ cells/mL, although the number of cells is large thereby the amount of the produced protein is large, HCP such as cell debris, etc. is also produced in a large quantity, and there is a problem in that it is difficult to remove HCP to a concentration corresponding to the pharmaceutical standards in the purification process.

In addition, in the fed-batch culture of the present invention, a supplement may be supplied to a basic culture medium for protein production. Examples of supplements include ActiCHO (GE Healthcare), Cell Boost (GE Healthcare), FM (Functional MAX, Gibco), yeast extract, Phytone UF (BD Biosciences), DM 19, PP3, TC Yeastolate UF (BD Biosciences), etc., and the above supplement may be ActiCHO, Cell Boost, and FM. The supplement may be added in appropriate amounts for the production of high levels of recombinant protein, and these can be used either individually or mixed.

The culture for producing rhTSH according to the present invention may be maintained for 10 to 20 days, specifically 11 to 15 days, and more specifically 12 to 18 days. According to a specific embodiment of the present invention, it may last for 12 days.

Figure 1A:
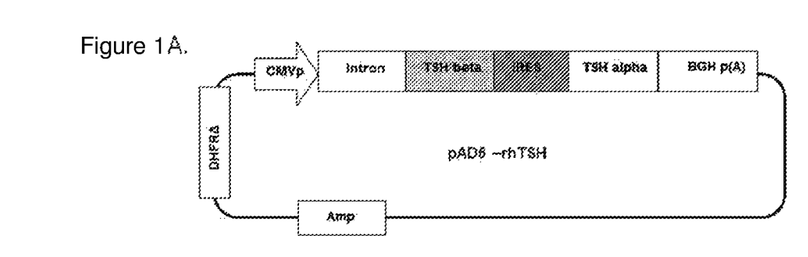
FIGS. 1A and 1B are the rhTSH expression vector prepared according to the present invention (FIG. 1A) and a graph showing the results of a long-term stability test of a cell line comprising the same (FIG. 1B).
Figure 1B:
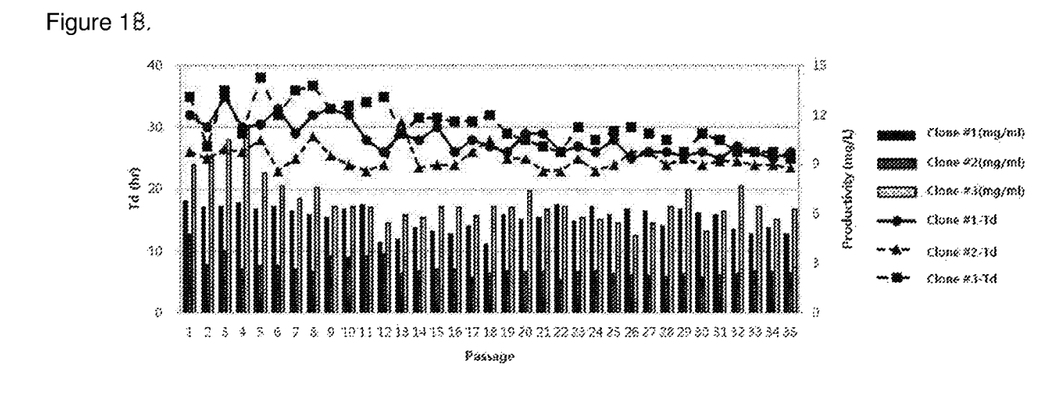

In order to produce rhTSH which maintains high purity and good quality in the fed-batch culture method, the inventors of the present invention prepared a vector capable of expressing the α subunit and β subunit of rhTSH transformed the same into a CHO cell line to select monoclonal cells expressing rhTSH at a high level, and named the selected single cell clones #1, #2, and #3, respectively (FIG. 1A and FIG. 1B).

Figure 2A:
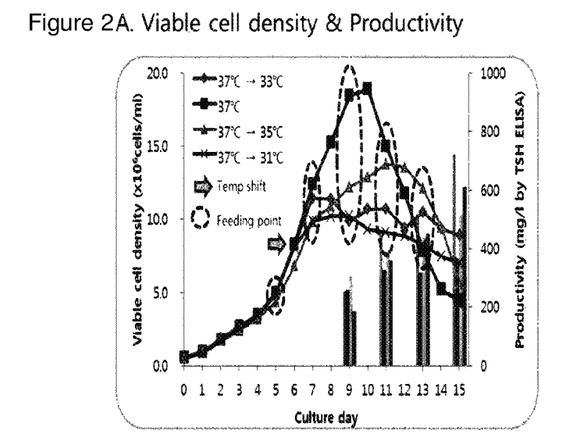
Figure 2B:
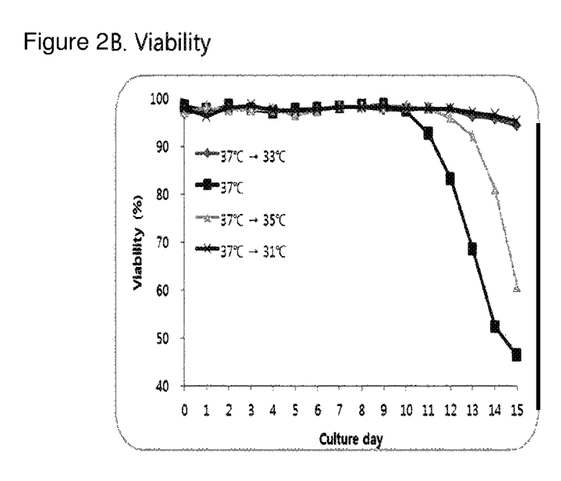

Using the selected cells, a fed-batch culture method with high productivity of rhTSH was established. When the culture temperature was lowered to 33° C. from the day 7 of the culture after culturing at 37° C. up to day 6 of the culture, it was confirmed that the viable cell density and productivity of rhTSH were increased (FIGS. 2A and 2B).

In addition, as a result of confirming the productivity of rhTSH depending on the number of cells, the production of rhTSH also increases as the number of cells increases, but when the number of cells exceeds $1.1 \times 10^7$ cells/mL upon temperature conversion, not only the production of rhTSH as well as impurities increased (Table 1).

Next, a method for purifying rhTSH in the rhTSH-expressing cell line cultured in the established production method was established. Specifically, when a series of affinity chromatography, depth filtration, diafiltration, and anion exchange chromatography were performed in order wherein the TSH-specific antibody collected from the cell supernants is used as a stationary phase, for the affinity chromatography, a high protein yield and purity compared to the conventional rhTSH purification method were shown, and the amount of impurities in the purified protein decreased within the standard values for pharmaceutical use (FIGS. 5A to 6B), and in terms of activity, it was confirmed to be similar to rhTSH (Thyrogen®) which is currently on market (FIG. 7A and FIG. 7B).

Therefore, in the fed-batch culture method according to the present invention, the production process is simple and economical as well as the activity and quality of the produced rhTSH are excellent. Accordingly, the rhTSH produced by the above-described method can be useful for the diagnosis and treatment of recurrent thyroid cancer.

The present invention also provides a method for treating a disease by administering a composition comprising the rhTSH of the present invention as a pharmaceutically active ingredient.

Such a method comprises administering an effective amount of a composition according to the present invention to a mammal in a healthy state directly associated with or not associated with the disease of interest. For example, the rhTSH may be administered to a subject, preferably a mammal, including a human, in a therapeutically effective amount.

The administration route and dosage of the composition according to the present invention may be administered to a subject in various ways and amounts depending on the disease to be treated, the presence or absence of side effects. The optimum administration method and dosage may be determined through routine experimentation.

The composition may be administered in combination with other drugs or physiologically active substances having a therapeutic effect on the disease to be treated, or it may be formulated in the form of a combination preparation with other drugs.

The present invention also provides a method for diagnosing recurrent thyroid cancer by administering a composition comprising rhTSH of the present invention.

In the above method, after administering the rhTSH of the present invention, radioactive iodine is administered, and recurrent thyroid cancer may be diagnosed through diagnostic scanning or the serum thyroglobulin (Tg) test.

The administration route and dose of the composition according to the present invention for diagnosis of recurrent thyroid cancer may be administered to a subject in various ways and amounts depending on the disease to be treated and the presence or absence of side effects, and the optimal mode of administration and dosage may be determined through routine experimentation.

MODE FOR THE INVENTION

Hereinafter, the present invention is explained in detail by Examples. The following Examples are intended to further illustrate the present invention without limiting its scope.

EXAMPLE 1

Preparation of Recombinant Human TSH (rhTSH) Expression Vector and Transformation The inventors of the present invention prepared an expression vector for producing rhTSH in a high yield.

Specifically, a gene fragment including the β subunit of rhTSH, and the genes of IRES and an α subunit of rhTSH were synthesized using Top Gene Technologies (Canada). After cloning the synthesized gene into pAD5 (Genexine) vector using EcoRI and XhoI restriction enzymes, it was named pAD-rhTSH.

As a result, an expression vector having a structure as shown in FIG. 1A was produced.

The above expression vector was prepared by transforming into a host cell using a method well-known in the conventional technical field. As such, in order to isolate vectors, EndoFree plasmid purification kit (Qiagen, USA) was used, and cells which expressed rhTSH at high yield were prepared using isolated vectors.

EXAMPLE 2

Preparation of a Single Cell Clone Expressing rhTSH in High Yield

Cells capable of expressing rhTSH at a high yield from the pAD-rhTSH expression vector prepared in Example 1 were prepared as follows.

Specifically, after the pAD-rhTSH expression vector was transformed into the CHO DG44 (−) DHFR (From Dr. Lawrence Chasin, Columbia University, USA) cell line under several conditions, under optimized conditions, the transformed cells were cultured for 48 hours in a basic medium including HT (hypoxanthine and thymidine) in a 6-well plate. Afterwards, the cells were cultured for 14 days in a medium not containing HT, and the culture scale increased from a 6-well plate to a 125-mL flask during this period. Cell clones expressing rhTSH at a high level were selected using the TSH-specific ELISA kit (Genway Biotech, USA).

The selected clones were cultured for 14 to 28 days in a medium containing 10 nM methotrexate (MTX) in 125-mL flasks, and a flask expressing rhTSH at the highest level was selected and the cells were inoculated to 20 wells of a 96-well plate. After culturing for 14 days, a single colony expressing a relatively high level of rhTSH was selected using an image cloner. The selected single colony was scaled from the 96-well plate to a 6-well plate and cultured for 21 to 27 days. In the cultured cells, the rhTSH productivity was measured again with the TSH-specific ELISA kit. The above process was repeated while increasing the concentration of MTX to 20 nM, 50 nM, 100 nM, and 200 nM, and finally the monoclonal cells with the highest rhTSH productivity were selected and amplified. The selected cells were selected as candidates for the research cell bank (RCB) and cultured up to 35 passages to confirm the stability during long-term culture, and Td (double time), the productivity and cell morphology of rhTSH were confirmed for every passage.

As a result, three RCB clones #1, #2, and #3 were selected as shown in FIG. 1B.

EXAMPLE 3

Establishment of Cell Culture Method for Production of rhTSH

An optimal cell culture method for the production of rhTSH was established for the three RCB clones selected in Example 2 above. Thyrogen®, rhTSH currently being sold only by a company called Genzyme, is known to be relatively unstable in solutions, and perfusion culture is used for the production thereof. Compared with other culture methods, perfusion culture has relatively low productivity, and its process is complicated and costly. Production yield of Thyrogen® of Genzyme produced by perfusion culture is known as 20 to 30 mg/L. Meanwhile, in the case of the fed-batch culture, the productivity is relatively high compared to the perfusion culture, the process is less complicated, and there is also an advantage that rhTSH is maintained at good quality in the culture process. Therefore, an attempt has been made to establish valuable culture conditions for the production of rhTSH. Since it is known that its protein stability in the solution form is influenced by various factors such as temperature, pH, cell viability, culture period, etc., the optimum conditions for the fed-batch culture were established by comparing with the quality of Thyrogen® of Genzyme (hereinafter referred to as "control group").

3.1. Establishment of Optimum Temperature

Cells were cultured under various temperature conditions to establish the optimum temperature for the production of rhTSH.

First, $0.5 \times 10^5$ cells/mL of clone #3 selected in the above Example 2 was cultured at 37° C. for 15 days in a Hycell CHO medium (Hyclone, USA), and in this case, on culture days 5, 7, 9, 11, and 13, 0.5% ActiCHO (GE Healthcare, USA) and 4% Cell Boost 5 (CBS, GE Healthcare, USA) were added as supplements. After 6 days, and it was cultured until day 15, when the viable cell density reached $6 \times 10^6$ to $8 \times 10^6$ cells/mL, the temperature was lowered to 37° C., 35° C., 33° C., and 31° C.

Viable cell density, cell viability, pH, glucose, lactate, glutamine, and glutamate were measured daily, and the rhTSH productivity was measured on days 9, 11, 13 and 15 as described in Example 2 above.

As a result, as shown in FIG. 2B, the viability of the cells cultured at 37° C. by day 15 is 50% or less, and the cells cultured at a temperature of 37° C. and then changed to 35° C. (37° C.→35° C.) were approximately 60%. On the other hand, the cells cultured at 37° C.→33° C. or at 37° C.→31° C. had a cell viability of 95% or more.

Meanwhile, as shown in FIG. 2A, as to the rhTSH productivity on day 15 of the culture, the cells cultured at 37° C.→33° C. showed the highest productivity of 0.7 g/L.

Therefore, the temperature for the production of rhTSH of 37° C. and then lowered to 33° C. was set as optimum culture conditions. In this case, after culturing at 37° C. for 6 days, culturing can be carried out while lowering the temperature to 33° C. from day 7.

3.2. Establishment of Optimal Cell Number

In the above Example 3.1, temperature conditions for the production of rhTSH were established. However, in order to confirm the effect of the viable cell density on the production of rhTSH at the time of lowering the temperature, the following experiment was conducted.

Specifically, when the density of viable cells is $6.0 \times 10^6$, $8.5 \times 10^6$, $9.8 \times 10^6$, $10.5 \times 10^6$, $11.5 \times 10^6$, or $12.0 \times 10^6$ cells/mL, respectively, all the experiments were carried out in the same manner as in the Example 3.1 above except that the culture temperature was lowered to 33° C. from 37° C. After culturing, the rhTSH production rate in the cell culture solution was measured in the same manner as in Example 2, and the purity of rhTSH was confirmed using the SDS-PAGE electrophoresis and Coomassie blue staining.

Meanwhile, HCP was confirmed by measuring absorbance. Standard samples with concentrations of 0, 1, 4, 20, 75, and 250 ng/mL were prepared for absorbance measurements. In addition, the rhTSH sample obtained under each condition was diluted according to the standard range, and mixed samples were prepared by mixing 120 μL of the above diluted rhTSH and 30 μL of the standard sample at a concentration of 250 ng/mL. The mixed sample was dispensed by 50 μL into two wells of an ELISA strip and 200 μL of Anti-CHO:Alkaline phosphatase was added. It was sealed, stirred at 24° C. and 180 rpm for 2 hours, washed four times with the washing solution, and then 200 μL of PNPP was added and allowed to react for 1 hour 30 minutes at room temperature to measure the absorbance thereof at a double wavelength of 405/492 nm.

At the time of changing the culture temperature, the production rate, the purity of rhTSH, and the amount of the host cell protein (HCP) as impurities depending on the density of viable cells were measured and shown in Table 1 below.

TABLE 1

| Viable cell density when changing temperature (cells/mL) | Maximum viable cell density (cells/mL) | HCP (PPM) | Production rate of rhTSH (g/l) | Purity of rhTSH (%) |
|---|---|---|---|---|
| $6.0 \times 10^6$ | $12.0 \times 10^6$ | 75,000 | 0.582 | 51.27 |
| $8.5 \times 10^6$ | $13.2 \times 10^6$ | 113,658 | 0.656 | 49.46 |
| $9.8 \times 10^6$ | $15.0 \times 10^6$ | 114,364 | 0.600 | 48.56 |
| $10.5 \times 10^6$ | $14.9 \times 10^6$ | 95,460 | 0.631 | 49.08 |
| $11.5 \times 10^6$ | $16.3 \times 10^6$ | N/A | N/A | N/A |
| $12.0 \times 10^6$ | $16.5 \times 10^6$ | N/A | N/A | N/A |

Figure 3:
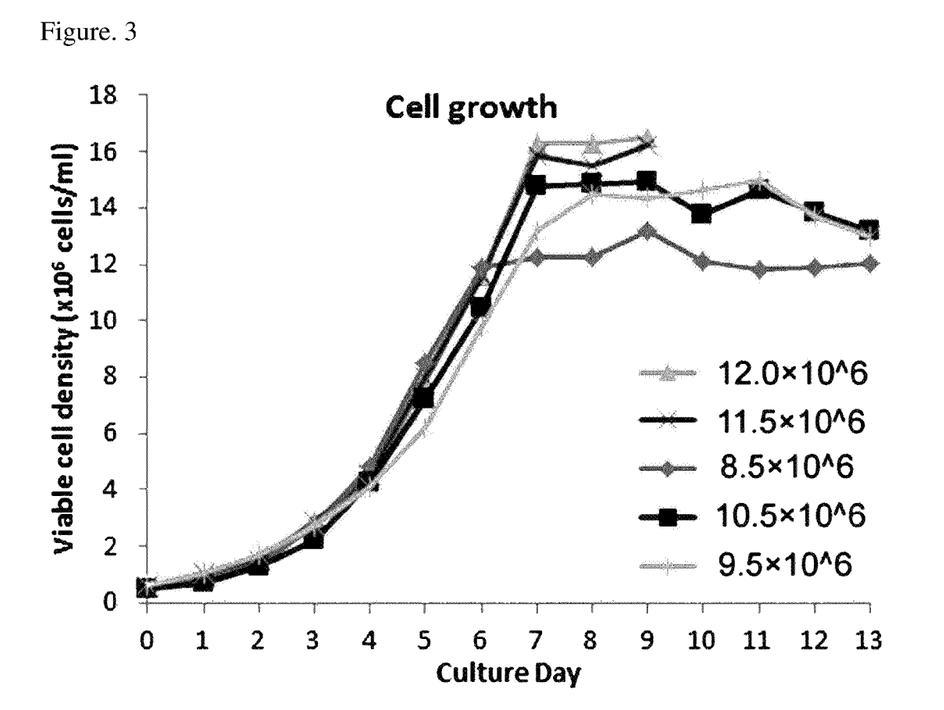
FIG. 3 is a graph showing the viable cell density depending on the number of cells when the temperature is lowered during the culturing process.

As a result, as shown in Table 1 above and FIG. 3, when the density of viable cells was in a range of $6.0 \times 10^6$ to $11.0 \times 10^6$ cells/mL at the time of changing the culture temperature, similar levels of the production rate and purity of rhTSH were shown. However, when the density of viable cells exceeded $11.0 \times 10^6$ cells/mL at the time of changing the temperature, HCP was contained in an excessive amount, and thereby, the production rate and purity of pure rhTSH could not be measured.

Therefore, from the above, it was confirmed that when the density of viable cells was $6.0 \times 10^6$ to $11.0 \times 10^6$ cells/mL, the culture temperature can be lowered to produce rhTSH with high yield and high purity.

Comparing to the case where the culture temperature is lowered at the density of the viable cells of $8.5 \times 10^6$ cells/mL, in the case where the culture temperature is lowered at the density of $6.0 \times 10^6$ cells/mL, it was confirmed that the production rate decreases by 1.12 times, but the amount of HCP decreased by 1.5 times or more. Since it is very important to reduce the amount of HCP in the production of pharmaceutical products, an optimal condition was set to lower the culture temperature when the viable cell density is $6.0 \times 10^6$ cells/mL which is a condition where the amount of HCP is minimum relative to productivity.

Meanwhile, in order to confirm whether lowering the culture temperature when the density of viable cells is $6.0 \times 10^6$ cells/mL affects the cell viability, in the 3 clones, experiments were conducted in the same manner as in Example 3.1 above, except that the culture temperature was lowered when the density of the viable cells was $6.0 \times 10^6$ cells/mL. The measurement results of the viable cell density of the cultured cells are shown in FIG. 4.

Figure 4:
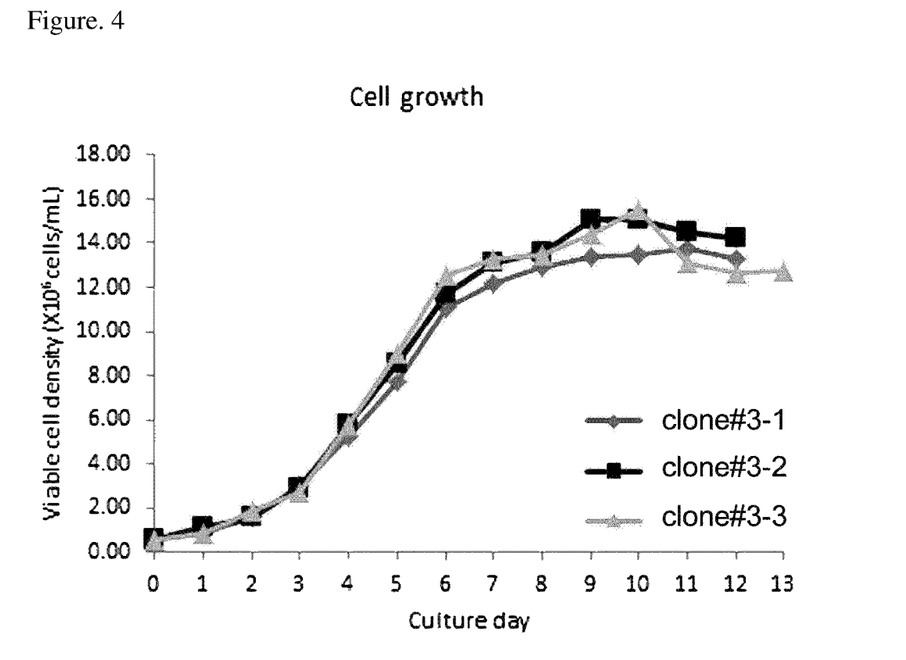
FIG. 4 is a graph showing the viable cell density of cells as the culture temperature is lowered, when the number of cells is 6×10⁶ cells/mL.

As a result, as shown in FIG. 4, although the culture temperature was lowered at $6.0 \times 10^6$ cells/mL, the cell viability was not affected, and the final cell density increased to $14.0 \times 10^6$ cells/mL.

3.3. Establishment of Optimum Culture Period

In order to establish an optimal culture period for the production of rhTSH, the viable cell density, cell growth rate, and rhTSH productivity were confirmed during the culture period of 18 days as described above.

As a result, the cell growth rate was 90% or more on day 18 of the culture, and the rhTSH productivity appeared higher than 1 g/L, but the quality was lower than that of the control group.

Therefore, the optimal fed-batch culture time which can maintain the productivity and the quality of the produced rhTSH is set to 12 days, and in conclusion, the fed-batch culture conditions for rhTSH production through the above-mentioned series of experiments were established.

The cells cultured under the conditions established in the present invention produced rhTSH of 0.6 g/L or more on day 12 of the culture, and it was found that the productivity increased 20 times or more while as comparable quality was maintained equivalent to the control group.

COMPARATIVE EXAMPLE 1

Conventional Method for Purifying rhTSH Protein

Gonadotropin is a glycoprotein polypeptide hormone secreted from the anterior pituitary gland of a vertebrate and includes follicle-stimulating hormone (FSH), luteinizing hormone (LH), human chorionic gonadotropin (hCG), and TSH, which have the identical α subunits and specific β subunits. Therefore, in general, purification of the rhTSH protein is carried out in the same way as the purification method of gonadotropin. Therefore, in order to compare purification yield and purity of the purified protein according to the conventional purification method with those of the purified protein according to the present invention, the rhTSH protein was purified according to the conventional purification method.

Specifically, the supernatant of cells cultured under the conditions established in Example 3 was collected and filtered using Millistak+DOHC and Millistak+XOHC filters in order. The filtered supernatant was ultrafiltered with a Pod Depth filter and XOHC, concentrated 20 times, and then subjected to diafiltration in A buffer (50 mM CHES, 40 mM NaCl, pH 10.0) using a 0.22 μm Millipak 20 filter. The filtered supernatant was subjected to anion exchange chromatography using Nuvia Q resin and eluted with 350 mM NaCl. Afterwards, it was then filtered again with a Pod Depth filter to remove insoluble aggregates. The filtered supernatant was equilibrated with B buffer (10 mM sodium phosphate, pH 7.0) and then subjected to a second purification with Blue 6 FF resin and 530 mM NaCl elution solution. Hydrophobic interaction chromatography using phenyl HP resin was used for the third purification, and the eluate subjected to the purification process above was passed through the Q membrane with C buffer (20 mM sodium phosphate, pH 7.0). The final product was formulated with D buffer (20 mM sodium phosphate, 3% mannitol, 0.2% NaCl). Proteins purified in this manner were subjected to SDS-PAGE electrophoresis and confirmed using Coomassie blue staining.

Figure 5A:
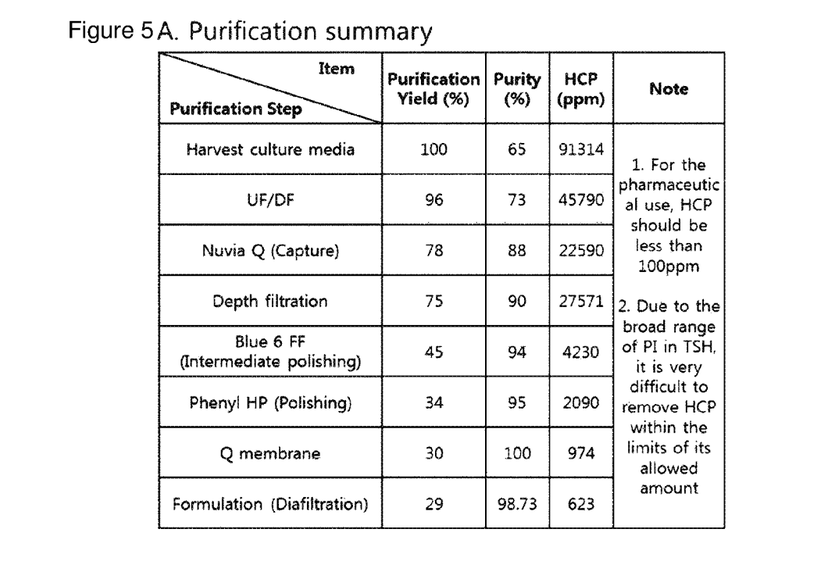
FIGS. 5A and 5B are a simple summary of the conventional rhTSH purification method (FIG. 5A) and a diagram showing SDS-PAGE results of the protein purified by a conventional method (FIG. 5B).
Figure 5B:
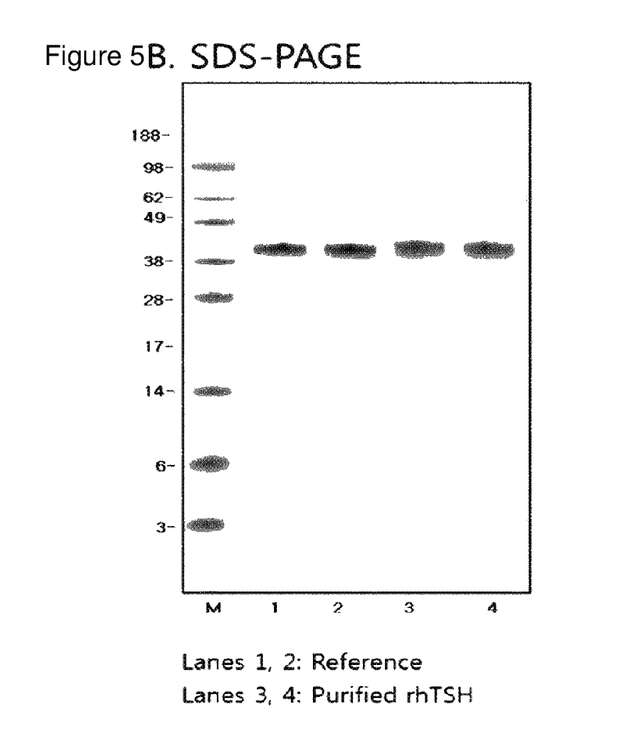

As a result, as shown in FIG. 5A and FIG. 5B, the rhTSH protein purified by the above method showed a yield of 30% or more and a purity of 98% or more, but the host cell protein (HCP) which is an impurity from the host cell was confirmed to be 1,000 ppm or more. Protein impurities for pharmaceutical use were below 100 ppm and additional procedures were required to remove them.

EXAMPLE 4

Establishment of High-Yield rhTSH Protein Purification Method

In general, the rhTSH protein has a wide range of PI values, and since there are 3 N-glycosylation sites, removal of impurities is not easy. Therefore, purification conditions for efficient purification of the rhTSH protein were established.

First, a column using an anti-gonadotropin antibody (ThermoFisher Scientific) as a stationary phase was prepared with the CaptureSelect system (ThermoFisher Scientific), and the cell supernatant prepared in the same manner as in Comparative Example 1 was loaded to the column at 3 g of protein/L CaptureSelect amount at a flow rate of 40 L/h, and then eluted with the E buffer solution (0.1 M sodium citrate, pH 3.0) being injected into the column at a flow rate of 40 L/h. Thereafter, it was filtered with a Pod Depth filter using an F buffer (50 mM Tris, pH 9.0) for removal of insoluble aggregates and HCP under a pressure of 3.0 bar or less at a flow rate of 86 mL/m² or less. The filtrate was dialyzed with a semipermeable membrane (Millipak 20, Millipore) with a pore size of 0.22 μm under a pressure of 1.0 bar or less, which was terminated when the conductivity of the filtrate became 30.0 μS/cm or less. The diafiltered purified intermediate product was loaded on a Capto adhere column at 15 mL/min and then eluted with the G buffer (20 mM sodium acetate, pH 3.8) at a flow rate of 15 mL/min. Finally, the eluate was formulated with the D buffer. Proteins purified in this manner were subjected to SDS-PAGE electrophoresis and confirmed using Coomassie blue staining.

Figure 6A:
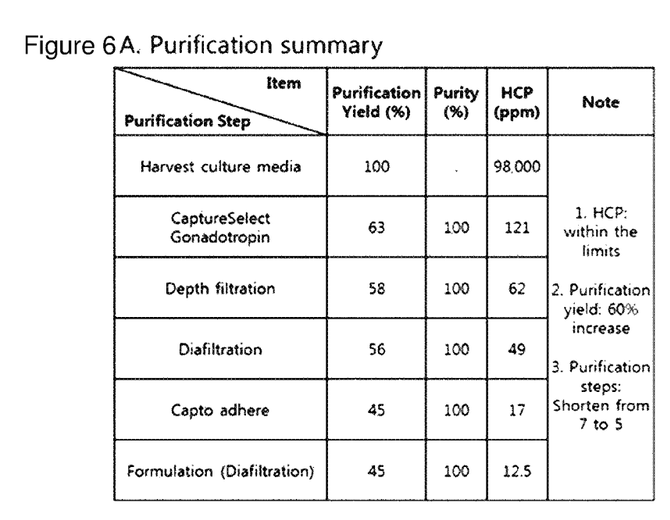
FIGS. 6A and 6B are a simple summary of the rhTSH purification method produced according to the method of the present invention (FIG. 6A) and a diagram showing the result of SDS-PAGE of the protein purified by the method of the present invention (FIG. 6B).
Figure 6B:
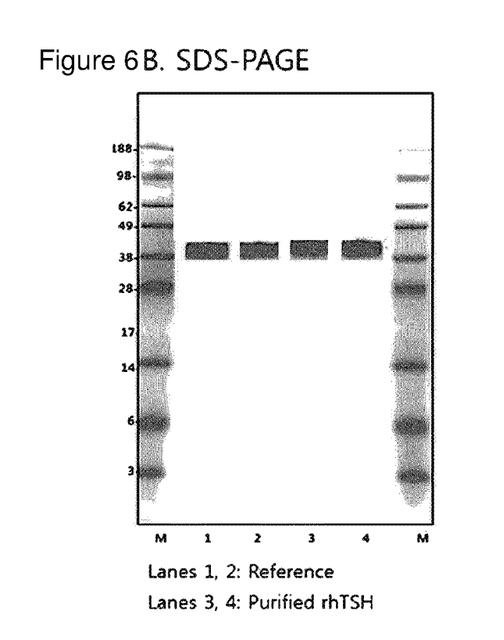
Figure 7A:
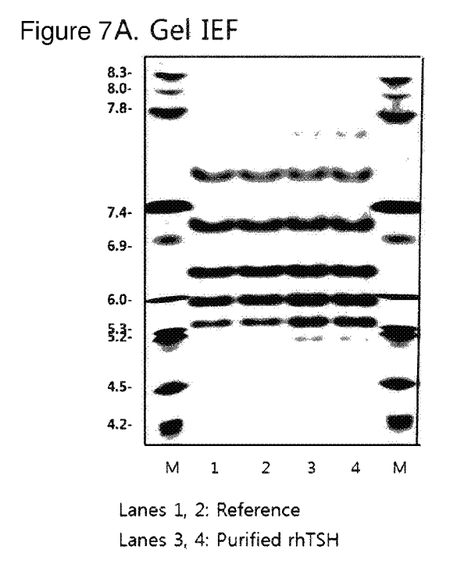
FIGS. 7A and 7B are diagrams showing the results of executing isoelectric focusing (IEF) analysis (FIG. 7A) and peptide mapping (FIG. 7B) for analyzing the quality of rhTSH produced according to the method of the present invention.
Figure 7B:
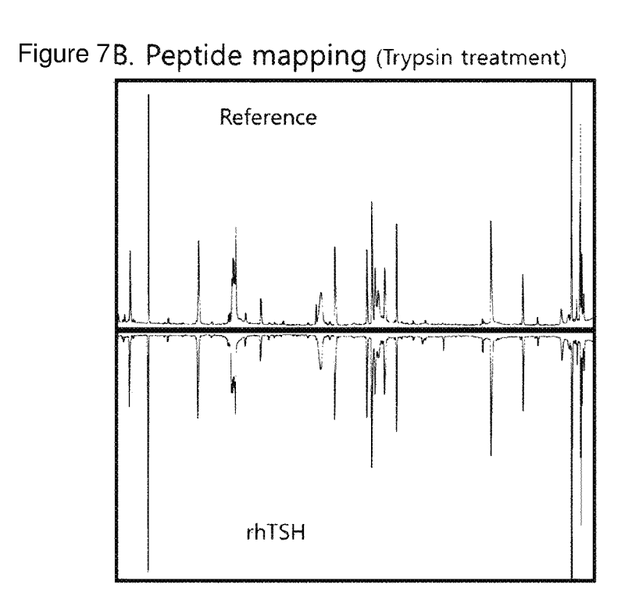

As a result, as shown in FIGS. 6A and 6B, the purified rhTSH protein without performing the Capto adhere step showed nearly 100% purity and most of HCP was removed, but it was confirmed that the amount exceeded 100 ppm which is an acceptable range for pharmaceutical use. However, the purified rhTSH protein after performing the Capto adhere step was confirmed, and as a result, it was possible to obtain a final product with an HCP of less than 20 ppm, and in this case, it was confirmed that the purification yield was 45% which was very excellent.

EXAMPLE 5

Quality Analysis of Purified rhTSH Protein

The main objective for establishing the production process of rhTSH protein is to increase the productivity of the protein under the fed-batch culture conditions. When culturing cells for the production of rhTSH for 18 days under the conditions according to the present invention, the productivity of the protein was very excellent, but there was a problem that the quality of the protein declined. Therefore, the rhTSH protein cultured for 12 days was subjected to isoelectric focusing profile (IEF) and peptide mapping and compared with the commercially available control group.

First, the glycosylation profiles of the refined rhTSH and the control group were compared on a gel-IEF. Samples were loaded on an IEF gel (Invitrogen) having a pH of 3 to 10, and electrophoresis was carried out sequentially for 1 hour at 200 V, 100 V and 500 V, respectively. Afterwards, the electrophoresed gel was confirmed by Coomassie blue staining.

Meanwhile, the patterns of peptide mapping of the purified rhTSH and the control group were analyzed by trypsin treatment. Specifically, 20 μL of 8 M urea (Sigma) and 2.5 μL of 200 mM DTT (Sigma) were added to a 100-μg sample and homogeneously equilibrated, followed by reaction at 70° C. for 10 minutes. Thereafter, 2.5 μL of 550 mM iodoacetamide (Sigma) was placed in each reaction tube and left at room temperature for 40 minutes. After treating 50 μL of trypsin (Promega) and 105 μL of 100 mM ammonium hydrogen carbonate (Sigma) to the sample and reacting at 37° C. for hours, the cleaved peptides were analyzed by ultra-performance liquid chromatography (UPLC).

As a result, as shown in FIGS. 7A and 7B, the rhTSH protein cultured and purified by the method of the present invention showed IEF profile and peptide mapping analysis results similar to the commercially available control group, and it was confirmed that the quality of the rhTSH protein of the present invention was excellent.

EXAMPLE 6

Confirmation of Physiological Activity of Purified rhTSH Protein

In order to confirm in vitro or in vivo activity of the rhTSH protein purified by the above-mentioned method, the following experiment was conducted.

6.1. Confirm In Vitro Activity of rhTSH Protein

To confirm the in vitro activity of the rhTSH protein, the expression of cAMP, a second messenger induced by the TSH/TSHR signaling pathway, was measured.

Specifically, the cAMP Hunter™ CHO-K1 TSHR (L) Gs cell line (DiscoverRx), which stably expresses thyrotropin receptor (TSHR) and cAMP-dependent luciferase gene, was cultured in a medium used for the culture of the same (Discover Rx) to maintain approximately 70 to 80% confluency before dispensing in a 96-well plate. The cultured cells were dispensed in a 96-well plate to 2×10$^4$ cells/well and cultured at 37° C. for 18 to 20 hours, then the medium in each well was removed, and 45 μL of the cAMP antibody reagent was added. 15 μl of the solution diluted with 3-isobutyl-1-methylxanthine IBMX) was added thereto and reacted at 37° C. for 30 minutes. 40 μL of the ED/CL solution was added thereto and reacted at 26 to 28° C. for 1 hour, and the ED/CL solution was prepared by mixing the ED reagent, HitHunter cAMP XS+Kit Substrate 2, HitHunter cAMP XS+Kit Substrate 1, and a cell dissolution reagent at a ratio of 15:1:5:9. Thereafter, 40 μL of the EA solution was added and reacted at 26 to 28° C. for 1 hour, and the relative light unit (RLU) was measured by a luminometer (BioTek, synergy2). As result values, $EC_{50}$ of the rhTSH protein and the control group was calculated and compared.

Figure 8A:
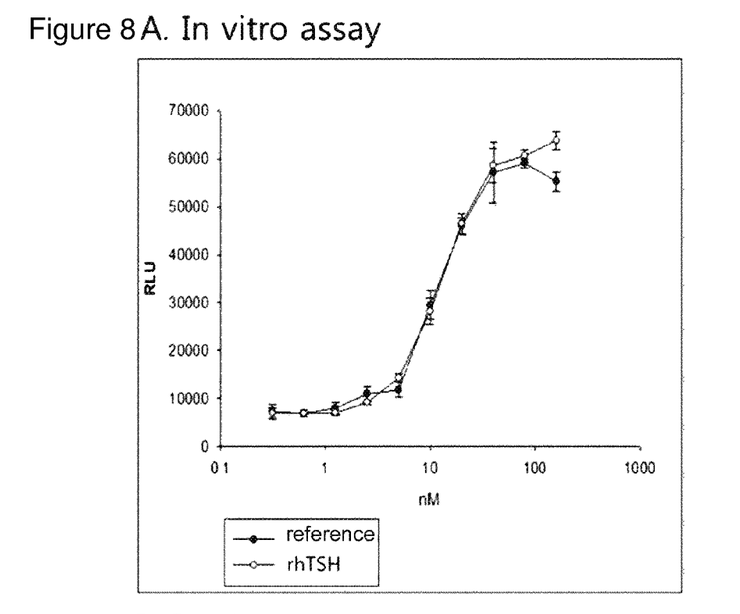
FIGS. 8A and 8B are graphs showing the results of confirming the in vitro activity (FIG. 8A) and in vivo activity (FIG. 8B) of rhTSH produced according to the method of the present invention.

As a result, as shown in FIG. 8A, it was confirmed that the $EC_{50}$ value of the rhTSH protein of the present invention was about 99% similar to the control group.

6.2. Confirmation of In Vivo Activity of rhTSH Protein

In order to confirm the in vivo activity of the rhTSH protein, the amount of T4 in the blood was measured when rhTSH was administered to an animal model.

First, general C57BL/6 mice were prepared and divided into groups having 4 mice each, which were injected intraperitoneally with each of rhTSH of the present invention and the control group at concentrations of 0.1, 0.5, and 2 mg/kg, respectively. Blood was sampled from each mouse before administration, 6 hours and 12 hours after administration. The obtained samples were stored in a cryogenic freezer prior to analysis, and analyzed by confirming intravascular T4 levels using a TSH-specific ELISA kit (Genway) as described in Example 2 above, and the same was compared.

Figure 8B:
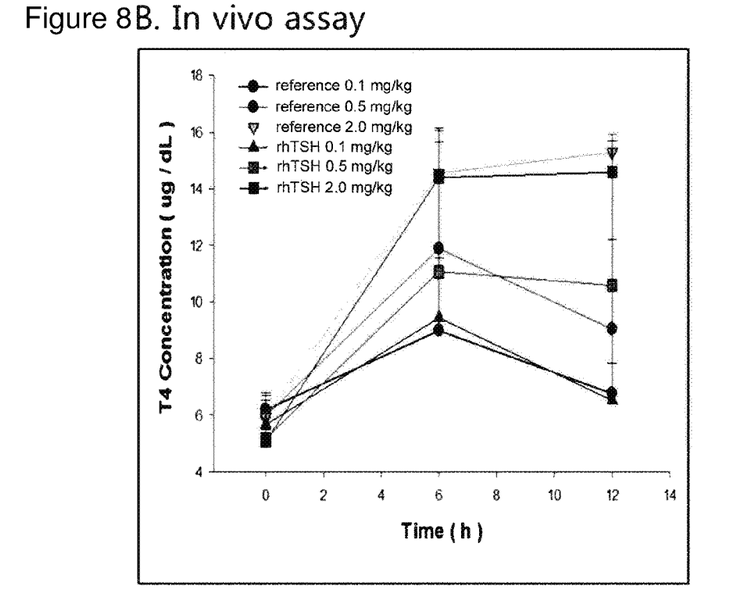

As a result, as shown in FIG. 8B, the rhTSH protein of the present invention induced the expression of T4 at a level similar to that of the control group in a concentration-dependent manner.

Therefore, since the rhTSH protein produced and purified by the method of the present invention showed similar activity as the commercially available product, it was found that the quality thereof was excellent.

The invention claimed is:

1. A method for producing purified recombinant human thyroid stimulating hormone (rhTSH) by fed-batch culturing, comprising the following steps:
   1) culturing a cell line producing rhTSH at a culture temperature of 36° C. to 38° C.;
   2) culturing the cell line at a culture temperature lowered to a range of 31° C. to 33° C., wherein the culture temperature is lowered when the number of cultured cells reaches $5 \times 10^6$ to $1 \times 10^7$ cells/mL; and
   3) separating rhTSH from the culture solution obtained in 2),
   wherein the step 3) comprises
      (a) subjecting the culture solution to an affinity chromatography and obtaining an eluate comprising the rhTSH, and
      (b) carrying out an anion chromatography on the eluate of (a); and
   wherein a content of host cell protein in the purified rhTSH is 100 ppm or less.

2. The method of claim 1, wherein the rhTSH comprises a polypeptide having the amino acid sequence of SEQ ID NO: 1 and a polypeptide having the amino acid sequence of SEQ ID NO: 2.

3. The method of claim 1, wherein the cell line producing rhTSH in step 1) comprises an expression vector that expresses a gene encoding an α subunit of rhTSH and a gene encoding a β subunit thereof.

4. The method of claim 1, wherein the cell line is any one selected from the group consisting of an immortal hybridoma cell, an NS/O myeloma cell, a 293 cell, a Chinese hamster ovary cell, a HeLa cell, a CapT cell, and a COS cell.

5. The method of claim 1, wherein the culture temperature of the step 1) is 37° C.

6. The method of claim 1, wherein the number of cells ranges from $6 \times 10^6$ to $8 \times 10^6$ cells/mL, when the culture temperature is lowered in the step 2).

7. The method of claim 6, wherein the number of cells is about $6 \times 10^6$ cells/mL.

8. The method of claim 1, wherein the culture temperature of the step 2) is about 33° C.

9. The method of claim 1, wherein, in the (a) of step 3), eluting the rhTSH from the affinity column chromatography is carried out using a sodium citrate solution of pH 1 to 5.

10. The method of claim 9, wherein the sodium citrate solution is of 0.01 to 5 M.

11. The method of claim 1, wherein the step 3) further comprises, after step (a),
   (c) subjecting an eluate containing the rhTSH obtained in (a) to a depth filtration, and
   (d) subjecting a filtrate obtained in (c) to diafiltration.

12. The method of claim 11, wherein, the (c) of step 3) is carried out at a pH of 6 to 12.

13. The method of claim 1, wherein, the content of HCP in the purified rhTSH is less than 20 ppm.

* * * * *

SEQUENCE LISTING

<160> NUMBER OF SEQ ID NOS: 2

<210> SEQ ID NO 1
<211> LENGTH: 92
<212> TYPE: PRT
<213> ORGANISM: Homo sapiens

<400> SEQUENCE: 1

Ala Pro Asp Val Gln Asp Cys Pro Glu Cys Thr Leu Gln Glu Asn Pro
1               5                   10                  15

Phe Phe Ser Gln Pro Gly Ala Pro Ile Leu Gln Cys Met Gly Cys Cys
            20                  25                  30

Phe Ser Arg Ala Tyr Pro Thr Pro Leu Arg Ser Lys Lys Thr Met Leu
        35                  40                  45

Val Gln Lys Asn Val Thr Ser Glu Ser Thr Cys Cys Val Ala Lys Ser
    50                  55                  60

Tyr Asn Arg Val Thr Val Met Gly Gly Phe Lys Val Glu Asn His Thr
65                  70                  75                  80

Ala Cys His Cys Ser Thr Cys Tyr Tyr His Lys Ser
            85                  90

<210> SEQ ID NO 2
<211> LENGTH: 118

```
<212> TYPE: PRT
<213> ORGANISM: Homo sapiens

<400> SEQUENCE: 2

Phe Cys Ile Pro Thr Glu Tyr Thr Met His Ile Glu Arg Arg Glu Cys
1               5                   10                  15

Ala Tyr Cys Leu Thr Ile Asn Thr Thr Ile Cys Ala Gly Tyr Cys Met
            20                  25                  30

Thr Arg Asp Ile Asn Gly Lys Leu Phe Leu Pro Lys Tyr Ala Leu Ser
        35                  40                  45

Gln Asp Val Cys Thr Tyr Arg Asp Phe Ile Tyr Arg Thr Val Glu Ile
    50                  55                  60

Pro Gly Cys Pro Leu His Val Ala Pro Tyr Phe Ser Tyr Pro Val Ala
65              70                  75                  80

Leu Ser Cys Lys Cys Gly Lys Cys Asn Thr Asp Tyr Ser Asp Cys Ile
            85                  90                  95

His Glu Ala Ile Lys Thr Asn Tyr Cys Thr Lys Pro Gln Lys Ser Tyr
            100                 105                 110

Leu Val Gly Phe Ser Val
            115
```